(12) United States Patent
Chudzik et al.

(10) Patent No.: US 8,143,043 B2
(45) Date of Patent: *Mar. 27, 2012

(54) ENCAPSULATED CELLS USING POSITIVELY-CHARGED INITIATOR POLYMER

(75) Inventors: Stephen J. Chudzik, St. Paul, MN (US); Ronald F. Ofstead, Maplewood, MN (US); Dale G. Swan, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 344 days.

This patent is subject to a terminal disclaimer.

(21) Appl. No.: 12/384,338

(22) Filed: Apr. 2, 2009

(65) Prior Publication Data

US 2009/0317887 A1   Dec. 24, 2009

Related U.S. Application Data

(63) Continuation of application No. 10/412,081, filed on Apr. 10, 2003, now Pat. No. 7,585,499.

(51) Int. Cl.
 *C12N 11/04* (2006.01)
 *C12N 5/00* (2006.01)
 *A61K 9/50* (2006.01)

(52) U.S. Cl. .................. 435/182; 424/93.7; 424/490

(58) Field of Classification Search .................. None
See application file for complete search history.

(56) References Cited

U.S. PATENT DOCUMENTS

| | | |
|---|---|---|
| 4,908,404 A | 3/1990 | Benedict et al. |
| 5,332,475 A | 7/1994 | Mechanic |
| 5,410,016 A | 4/1995 | Hubbell et al. |
| 5,529,914 A | 6/1996 | Hubbell et al. |
| 5,573,934 A | 11/1996 | Hubbell et al. |
| 5,834,274 A | 11/1998 | Hubbell et al. |
| 5,858,653 A | 1/1999 | Duran et al. |
| 6,007,833 A | 12/1999 | Chudzik et al. |
| 6,060,582 A | 5/2000 | Hubbell et al. |
| 6,258,870 B1 | 7/2001 | Hubbell et al. |
| 6,410,044 B1 | 6/2002 | Chudzik et al. |
| 7,427,415 B2 | 9/2008 | Scharp et al. |
| 7,585,499 B2 * | 9/2009 | Chudzik et al. .............. 424/93.7 |
| 7,820,158 B2 * | 10/2010 | Chudzik et al. .............. 424/93.7 |

FOREIGN PATENT DOCUMENTS

WO  WO 01/85180  11/2001

OTHER PUBLICATIONS

Schwanstecher, et al., (1994) *Photoaffinity Labeling of the Cerebral Sulfonylurea Receptor Using a Novel Radioiodinated Azidoglibenclamide Analogue*, Journal of Neurochemistry, 63: 698-708.

Aguilar-Bryan, et al., (1990) *Photoaffinity Labeling and Partial Purification of the β Cell Sulfonylurea Receptor using a Novel, Biologically Active Glyburide Analog*, Journal of Biological Chemistry, 265: 8218-8224.

Kramer, et al., (1988) *Direct Photoaffinity Labeling of the Putative Sulfonylurea Receptor in Rat β-cell Tumor Membranes by [$^3H$]-glibenclamide*, FEBS Letter., 229:355-359.

Seyfert et al., (1995) *Adhesion of leucocytes to microscope slides as influenced by electrostatic interaction*, Biomaterials, 16: 201-207.

Mellott et al., (2001) *Release of protein from highly cross-linked hydrogels of poly(ethylene glycol) diacrylate fabricated by UV polymerization*, Biomaterials 22:929-941.

Uludag, et al. (2000), *Technology of mammalian cell encapsulation*, Advanced Drug Delivery Reviews, 42: 29-64.

Hwang, et al. (1998) *Synthesis of sulfonylurea conjugated copolymer via PEO spacer and its in vitro short-term bioactivity in insulin secretion from islets of Langerhans*, Biomaterials,19: 1189-1195.

Park, et al., (2002) *Determination of the Specific Interaction between Sulfonylurea-Incorporated Polymer and Rat Islets*, Journal of Biochemistry, 131: 359-364.

Park, et al. (2001) *Interaction of sulfonylurea-conjugated polymer with insulinoma cell line of MIN6 and its effect on insulin secretion*, Journal of Biomedical Materials, 55:72-78.

Park, et al., (2001) *Incorporation of sulfonylurea into sugar-carrying polymers and their effects on insulin secretion from MIN6 cells in a solution state*, Journal of Biomaterials Sci. Polymer Edn., 12: 911-920.

Gopalakrishnan, et al., (2003) *Pharmacological characterization of a 1,4-dihydropyridine analogue, 9-(3,4-dichlorophenyl)-3,3,6,6-tetramethyl-3,4,6,7,9,10-hexahydro-1,8(2H,5H)-acridinedione (A-184209) as a novel $K_{ATP}$ channel inhibitor*, British Journal of Pharmacology, 138: 393-399.

Hastedt, (2003) *Inhibition of ATP-sensitive $K^+$-channels by a sulfonylurea analogue with a phosphate group*, Biochemical Pharmacology, 65: 599-602.

Cruise, et al. (1999), *In Vitro and In Vivo Performance of Porcine Islets Encapsulated in Interfacially Photopolymerized Poly(Ethylene Glycol) Diacrylate Membranes*, Cell Transplantation, 8: 293-306.

* cited by examiner

*Primary Examiner* — David Naff

(74) *Attorney, Agent, or Firm* — Kagan Binder, PLLC

(57) ABSTRACT

Positively-charged initiator polymers having a polymerization initiator group and a cationic portion are provided. The initiator polymers can be used with a polymerizable material for the formation of a polymeric matrix on a surface. The initiator polymers are particularly useful for cell encapsulation using macromers.

22 Claims, 1 Drawing Sheet

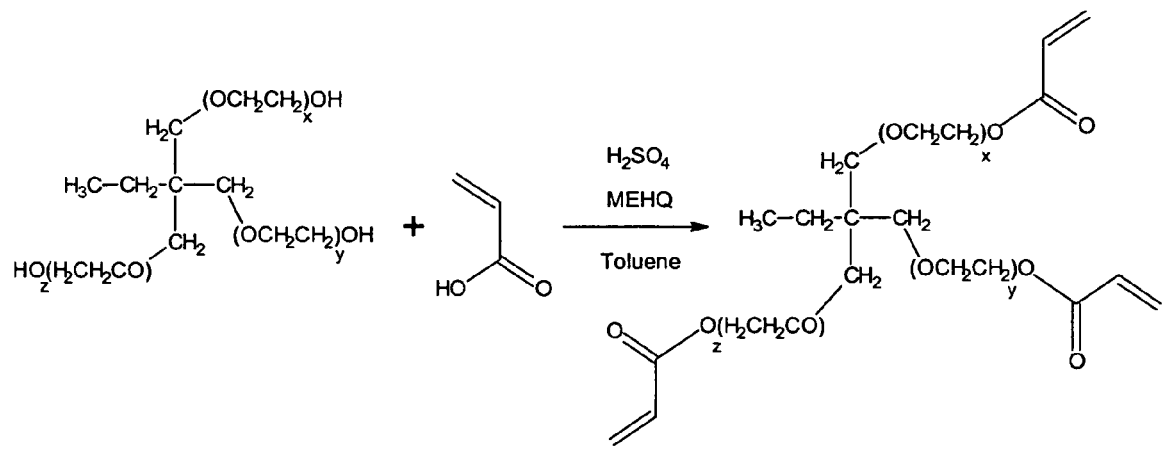
Compound II – PEG-triacrylate macromer

ENCAPSULATED CELLS USING POSITIVELY-CHARGED INITIATOR POLYMER

CROSS-REFERENCE TO RELATED APPLICATIONS

The present application claims the benefit of and is a continuation of commonly-owned U.S. Nonprovisional patent application Ser. No. 10/412,081, filed Apr. 10, 2003, now U.S. Pat. No. 7,585,499 titled CHARGED INITIATOR POLYMERS AND METHODS OF USE, the entire contents of which is incorporated herein by reference.

FIELD OF THE INVENTION

The current invention relates to compounds useful for forming a polymeric matrix on the surface of a substrate. More specifically, the invention relates to initiator polymers useful for forming a polymeric matrix on the surface of a biological substrate.

BACKGROUND

The use of polymeric material for the encapsulation of cells and tissue offers great potential for the treatment of diseases and other medical indications. Particularly useful applications involve utilizing polymeric material for encapsulating tissues or cells for transplantation into a patient in order to provide therapy. Although various techniques for encapsulating mammalian cells have been known for a number of decades and have been used in research settings, it is only more recently that cell encapsulation technologies have been applied for the potential treatment of diseases.

Cell encapsulation methods are generally aimed at surrounding a cell or group of cells with a material barrier in order to protect the transplanted encapsulated cells from host immune rejection. The material barrier around the cells ideally allows the cells to remain viable and to function properly in order to provide therapeutic value to the host. In order to perform this function, the material that is used to encapsulate the cells, which typically includes a polymeric compound, should be resistant to biodegradation and should be sufficiently permeable to allow for diffusion of cellular waste products, nutrients, and molecules involved in cellular responses. Preferably the material barrier is not permeable to certain host molecules, such as immunoglobulins and complement factors that could contribute to the destruction of the foreign cells.

Advances in cell encapsulation technologies have been focused on improving the permselectivity, mechanical properties, immune protectivity and biocompatibility of the material barrier that is formed around the cells. Various micro- and macroencapsulation techniques, including microencapsulation by polyelectrolyte complexation, thermoreversible gelation, interfacial precipitation, interfacial polymerization, and flat sheet and hollow fiber-based macroencapsulation have been studied and are reviewed by Uludag et al. *Adv. Drug Deliv. Rev.* 42:29-64 (2000).

One commonly used method for the encapsulation of cells is the alginate crosslinking method, which utilizes polyanionic alginate and polycationic polylysine polymers. Encapsulation by the alginate method typically occurs by the crosslinking of alginate via the $Ca^{2+}$ ion and the interaction of polylysine with the alginate molecules. Unfortunately, there are a number of problems associated with this approach to cell encapsulation. Such problems include the swelling of alginate microcapsules due to the presence of $Ca^{2+}$ in the inner alginate core, insufficient biocompatibility due to guluronic acid content in alginate/polylysine capsules, and insufficient mechanical strength of the alginate coating. Moreover, the process of alginate encapsulation is nonspecific and can result in the formation of microcapsules that do not contain the cells or cell groups intended to be encapsulated or that contain other non-target biological materials. Due to these problems, alternative methods for cell encapsulation have been investigated.

One promising alternative to alginate crosslinking is a method termed interfacial polymerization. Interfacial polymerization has the possibility of offering all of the advantages of the alginate encapsulation method for cellular encapsulation and its therapeutic applications, although there has been little done to investigate its potential. Interfacial polymerization generally involves the formation of a layer of polymerized material, such as synthetic or natural polymerizable polymers, on the surface of a biological substrate. The formation of the layer of polymeric material is generally promoted by the activation of a polymerization initiator, which is deposited on the surface of the biological substrate, in the presence of the polymerizable polymers.

Some polymerization initiators for use in interfacial polymerization methods have been demonstrated in U.S. Pat. No. 5,410,016 and U.S. Pat. No. 5,529,914. These patents describe depositing the polymerization initiator, eosin Y, on a cell membrane and then activating the initiator to promote polymerization of a macromer solution. However, the use of eosin Y, which is a relatively nonpolar, low molecular weight light-activated initiator dye, or compounds similar to eosin, presents many disadvantages for interfacial polymerization methods and also presents potential problems to subjects receiving transplanted encapsulated cells. For example, these dyes and other similar low molecular weight compounds present toxicity problems as they can penetrate into a cell and interfere with normal biochemical pathways. If penetrated into the cell, these dyes can cause free radical damage when activated by external sources of energy. Other drawbacks arise if the dye is able to diffuse out of the formed polymeric layer, thereby producing potential toxicity to a host organism. Dyes such as eosin also tend to aggregate in aqueous solution, thereby reducing the efficiency of the encapsulation process and introducing problems with reproducibility. Finally, in view of the limited efficiency of these dyes in initiating sufficient radical chain polymerization, it is often necessary to add one or more monomeric polymerization "accelerators" to the polymerization mixture. These accelerators also tend to be small molecules which are capable of penetrating the cellular membrane and have the potential to be cytotoxic or carcinogenic. Therefore, it is also desirable to minimize the use of these accelerators. In attempts to overcome the above problems, applicants have previously introduced novel interfacial polymerization reagents and techniques (see U.S. Pat. Nos. 6,007,833 and 6,410,044; herein incorporated by reference in their entirety).

Despite these teachings, improved initiators for interfacial polymerization methods are desired. The cell surface, to which the polymerization initiator is targeted, is very complex and presents a challenge for the design of initiators that function in a desired manner. For example, the cell surface contains numerous surface proteins, some of which have carbohydrate groups containing charged moieties, such as sulfated proteoglycans and glycosaminoglycans. It is desirable to design initiators that localize to the biological surface but do not affect the physiology of the cell in a negative manner. For example, improved initiators should preferably promote the formation of a polymeric layer on the cell surface in an efficient manner without triggering any detrimental cellular processes, such as signaling pathways that lead to cell death.

SUMMARY OF THE INVENTION

The current invention provides reagents and methods useful for the formation of a polymeric layer, also referred to herein as a "polymeric matrix" on the surface of a substrate. More specifically, the invention provides a positively-charged polymerization initiator polymer that is useful for the formation of a polymeric layer on negatively charged surfaces. The positively-charged polymerization initiator polymer is particularly useful for encapsulating cells and tissue with biocompatible polymers.

In one aspect, the positively-charged initiator polymer is used in a method to promote the polymerization of a polymeric material on a biological surface. The method involves providing a biological surface, which is typically the surface of a cell, group of cells, or a tissue intended to be coated with the polymeric material. The initiator polymer is then placed in contact with the biological surface. According to the invention, the initiator polymer includes (i) a polymerization initiator group, and (ii) a cationic portion that provides a positive charge to the polymer in conditions having a pH at least up to, and including, pH 8. The cationic portion can facilitate the solubility of the initiator polymer in an aqueous solution and also allows for the association of the initiator polymer with the cell surface. The cationic portion can be particularly advantageous in embodiments where the initiator polymer contains a plurality of initiator groups, which are typically nonpolar and confer a substantial degree of hydrophobicity to the initiator polymer. Preferably, the cationic portion also allows for the preparation of initiator polymers that have a weight average molecular weight ($M_w$) in the low to medium range, contain a plurality of initiator groups, and are soluble in an aqueous solution.

The method of forming a polymeric matrix also involves providing a polymerizable material to the biological surface. The polymerizable material is typically a polymerizable polymer (for example, a macromer) that can be applied before, during or after application of the initiator polymer. Suitable macromers include natural or synthetic polymerizable polymers that preferably provide the formed matrix with an acceptable degree of biocompatibility. After the biological surface has been contacted with the initiator polymer and the macromer, a source of energy is applied to the surface to activate the initiator group, thereby promoting the polymerization of the macromer on or near the biological surface. According to preferred embodiments, the energy source is provided by long UV wavelengths and more preferably visible light wavelengths. Polymerization can be direct or indirect, wherein indirect methods typically utilize an acceptor or reductant to promote free radical polymerization.

Cells, groups of cells, or tissue can be encapsulated using the positively-charged initiator polymer of the invention. Although the invention is not limited to any particular type of natural or synthetic material as the target surface, the positively-charged initiator polymer is particularly useful as a reagent that promotes the formation of an encapsulating matrix around cells. Encapsulated cells can be transplanted into a subject in order to provide a therapeutic effect. Such applications for the positively-charged initiator polymer include the encapsulation of pancreatic islets for transplantation into a subject having diabetes and in need of therapy.

In another aspect, the invention provides a positively-charged initiator polymer that includes (i) a photoinitiator group selected from the group of visible light-activated dyes, and (ii) a cationic portion that provides a positive charge to the initiator polymer in conditions having a pH at least up to, and including, pH 8. The photoinitiator group is coupled to the polymeric backbone of the initiator polymer, and, in preferred embodiments the cationic portion is provided by a cationic group that is also coupled to the polymeric backbone. Suitable photoinitiator groups include visible light-activated dyes such as acridine orange, camphorquinone, ethyl eosin, eosin Y, erythrosine, fluorescein, methylene green, methylene blue, phloxime, riboflavin, rose bengal, thionine, xanthine dyes, and the like.

Particularly useful initiator polymers include cationic groups that provide the initiator polymer with a positive charge in conditions having a pH at least up to, and including, pH 8; more preferably in conditions having a pH at least up to, and including, pH 10, and most preferably in conditions having a pH at least up to, and including, pH 12. Groups conferring these cationic properties can be selected from ternary and quaternary cationic groups such as quaternary ammonium, quaternary phosphonium, and ternary sulfonium groups. Particularly useful initiator polymers have a weight average molecular weight ($M_w$) in the low to medium molecular weight range, that is, less than about $3.2 \times 10^6$ Da. Preferred initiator polymers have a $M_w$ about 250,000 Da or less, 100,000 Da or less, and 50,000 Da or less. The initiator polymer includes one, and preferably more than one initiator group, and provides initiator activity capable of promoting the polymerization of polymers, (for example macromers) in the presence of a reductant. A particularly preferred initiator polymer includes (i) a polyamine backbone, (ii) a plurality of visible light-activated dyes coupled to the backbone, (iii) a plurality of quaternary ammonium groups coupled to the backbone, and (iv) a $M_w$ of less than about $3.2 \times 10^6$ Da.

The invention also provides a kit for providing a polymeric coating to a surface. The kit includes at least a positively-charged polymerization initiator polymer and a polymerizable material that can be used in conjunction with the initiator polymer. The initiator polymer of the kit includes: (i) a polymerization initiator group, and (ii) a cationic portion, wherein the cationic portion provides a positive charge to the polymer in conditions having a pH at least up to, and including, pH 8.

The invention also provides cells, groups of cells, and tissue encapsulated with a polymeric matrix using the positively-charged initiator polymer, as described herein.

BRIEF DESCRIPTION OF THE DRAWING

FIG. 1 illustrates a synthetic scheme for the preparation of a PEG-based macromer, PEG-triacrylate (Compound II).

DETAILED DESCRIPTION OF THE INVENTION

The present invention provides positively-charged initiator polymers, herein also referred to as "initiator polymers", compositions including the initiator polymers, and methods for performing the interfacial polymerization of polymerizable material on or near a surface using these initiator polymers. "Polymer" refers to a compound having one or more different repeating monomeric units and includes linear polymers and copolymers, branched polymers and copolymers, such as highly branched dendrimer polymers and copolymers, herein referred to as "dendrimers", graft polymers and copolymers, and the like. "Surface" broadly refers to any sort of natural or synthetic surfaces. Natural surfaces include "biological surfaces" which broadly refers to the surface of any sort of biological material, such as, for example, the surface of cells, or the surface of a group of cells, or the surface of a tissue. Synthetic surfaces include any useful man-made materials, such as functionalized and non-functionalized materials made of plastics, ceramic, resins, polysaccharides, silicon, or silica-based materials, glass, metals, films, gels, membranes, nylon, natural fibers such as silk, wool and cotton and polymers. In one embodiment, the surface has a negative charge and the positively-charged initiator polymer can be associated with this surface via opposite charges.

The initiator polymers are particularly useful for cell encapsulation methods although they can also be used to form a matrix of polymerized material on a biological surface in any sort of ex vivo or in vivo method. Cell encapsulation involves the formation of polymeric layer over all, or a portion of the surface of the cell, group of cells, or tissue. This polymeric layer typically has a certain physical and functional properties, such as thickness, permeability, strength, and protectivity. Optionally, the initiator polymers can be used to form a matrix of polymerized material on the surface of any type of natural or synthetic material.

According to the invention, positively-charged initiator polymers useful for providing a coating to a surface include at least one polymerization initiator group, and a cationic portion that provides a positive charge to the initiator polymer in conditions having a pH at least up to, and including, pH 8. The initiator group refers to a portion of the initiator polymer that can specifically accept energy and generate a free radical species, directly or indirectly, and is sufficient to promote free radical polymerization of polymerizable material. The cationic portion provides the initiator polymer with a positive charge in conditions having a pH at least up to, and including, pH 8; and, in some embodiments can provide the initiator polymer with a positive charge in conditions having a pH at least up to, and including, pH 10, and more preferably up to and including pH of 12. The cationic portion of the initiator polymer can be derived from a positively-charged polymeric backbone, from cationic groups pendent from the backbone, or both. In most embodiments, the cationic property of the initiator polymer is derived from cationic groups pendent from the polymer backbone. "Pendent groups" refer to one or more chemical groups coupled to the polymer backbone anywhere along its length, or chemical groups coupled at either terminus of the backbone, or both.

In one embodiment, the initiator polymer can be used in a step in a method for coating a biological surface, such as a cell encapsulation method. In these methods, the initiator polymer is used in conjunction with a surface to be coated and polymerizable material, such as macromers. In some embodiments the initiator polymer is applied to the cells separately from the macromer component; in other embodiments the initiator polymer and the macromer component are applied together as a polymerizable composition to the cells. Therefore, the invention also provides compositions that include a positively-charged initiator polymer and a macromer component. Compounds useful for cell encapsulation, such as reductants/acceptors and other polymerization enhancing components, for example, stabilizers, viscosity enhancing agents, and co-catalysts, can be introduced into the polymerization method in existing steps, in additional steps, or can be present as a reagent in a polymerizable composition. Therefore, the invention also provides polymerizable compositions and kits for forming a polymer coating on a surface that can include an initiator polymer, a macromer component, a reductant/acceptor, and a viscosity-enhancing agent.

In a more specific embodiment, the invention provides an initiator polymer that includes a visible light-activated photoinitiator group, and a cationic portion that provides a positive charge to the initiator polymer in conditions having a pH at least up to, and including, pH 8. The visible light-activated photoinitiator group can be selected from the group of visible light activated dyes such as eosin. In another specific embodiment, the invention provides an initiator polymer having a plurality of visible light-activated photoinitiator groups coupled to the polymer backbone, a plurality of ternary or quaternary cationic groups coupled to the polymer backbone, and a $M_w$ of less than $3.2 \times 10^6$ Da.

As used herein "weight average molecular weight" or $M_w$, is an absolute method of measuring molecular weight and is particularly useful for measuring the molecular weight of a polymer (preparation), such as preparations of initiator polymers and macromers. Polymer preparations typically include polymers that individually have minor variations in molecular weight. Polymers are molecules that have a relatively high molecular weight and such minor variations within the polymer preparation do not affect the overall properties of the polymer preparation (for example, the characteristics of an initiator polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemtporary Polymer Chemistry*; pg 271 (1990).

The invention also specifically provides the positively-charged initiator polymer as a component in a group of compounds used for interfacial polymerization methods, and methods for the treatment of particular diseases. These compounds and methods can be implemented for the encapsulation of cells or tissue, wherein the encapsulated cells or tissue are therapeutically useful. For example, pancreatic islets that are encapsulated using the initiator polymer of the invention can be transplanted to a diabetic patient in need of functional pancreatic tissue.

The positive charge provided by the cationic portion of the initiator polymer can allow the initiator polymer to be configured as a surprisingly effective polymerization initiator, particularly for cell encapsulation methods. In one aspect, the positive charge of the initiator polymer can afford the polymer with a high degree of solubility in an aqueous solution. This high degree of solubility in an aqueous solution can be maintained in embodiments wherein the initiator polymer has a plurality of initiator groups, which are typically nonpolar and confer a substantial degree of hydrophobicity to the initiator polymer per se. Therefore, the presence of the cationic portion can allow for the preparation of initiator polymers that can include a substantial number of initiator groups and function as polymerization initiators when the initiator groups are activated. This arrangement is particularly advantageous, as it has been discovered initiator polymers having a low to medium $M_w$ can be prepared and used in cell encapsulation processes while maintaining a high level of cell viability.

Therefore, according to the invention, the cationic portion of the initiator polymer allows for the preparation of initiator polymers that are soluble in an aqueous solution and that have a high degree of "initiator potential", referring to the ability of a particular compound to initiate the polymerization of polymerizable material. In this regard it is not necessary to increase the size of the initiator polymer to improve solubility in an aqueous solution.

In another aspect, the positive charge of the initiator polymer can also allow for its interaction with negatively charged surfaces, for example, negatively charged surfaces of biological material. Cell surface proteins that bear anionic charged groups typically impart a negative charge over the cell surface. Surface molecules such as glycosaminoglycans and sulfated proteoglycans contribute to the charged surface of a cell. However, other biological materials that have a negatively charged surface can also be suitable as surfaces that can associate with the initiator polymer of the invention. Therefore, the cationic portion of the initiator polymer provides a convenient way of localizing the initiator polymer to a target anionic surface, particularly a cell surface, during cell encapsulation process.

According to the invention, the initiator polymer includes one or more initiator groups that are coupled to the backbone of the initiator polymer. The initiator groups of the initiator polymer are able to promote free radical polymerization of polymerizable material, such as macromers, when the initiator groups are activated by an external source of energy. Activated initiator groups can cause free radical polymerization of the polymerizable material either directly or indirectly. Indirect methods typically include the transfer of energy from the activated initiator to an acceptor or reductant, a chemical species that can form a free radical and can act to cause polymerization of the polymerizable material. In direct methods the initiator group provides the free radical itself.

According to the invention, the initiator polymer can be localized to a negatively charged surface, such as the surface of a biological material. Upon activation of the initiator groups, polymerizable material that is in proximity to the initiator polymer polymerizes, leading to the formation of a layer of polymeric material, or a matrix, on the surface. This type of polymerization is typically referred to as interfacial polymerization.

The initiator polymer can include light-activated photoinitiator groups, thermally activated initiator groups, chemically activated initiator groups, or combinations thereof. Suitable thermally activated initiator groups include 4,4' azobis(4-cyanopentanoic) acid and 2,2-azobis[2-(2-imidazolin-2-yl)propane]dihydrochloride or other thermally activated initiators provided these initiators can be incorporated into an initiator polymer. Chemically activated initiation is often referred to as redox initiation, redox catalysis, or redox activation. In general, combinations of organic and inorganic oxidizers, and organic and inorganic reducing agents are used to generate radicals for polymerization. A description of redox initiation can be found in *Principles of Polymermization*, $2^{nd}$ Edition, Odian G., John Wiley and Sons, pgs 201-204, (1981). Redox initiators that are not damaging to biological systems are preferably used. Photoinitiator groups and thermally activated initiator groups that utilize energy that is not damaging to biological systems are preferably used. In one embodiment, photoinitiator groups having long wavelength UV and visible light-activated frequencies are coupled to the backbone of the initiator polymer. In a preferred embodiment, visible light-activated photoinitiators are coupled to the polymer backbone.

Photoinitiation can occur by various mechanisms, including Norrish type I reactions, intra- or intermolecular hydrogen abstraction reactions, and photosensitization reactions utilizing photoreducible or photo-oxidizable dyes. The latter two types of reactions are commonly used with an energy transfer acceptor or a reductant, which can be, for example, a tertiary amine. Such tertiary amines can be incorporated into the polymeric backbone of the macromer. In a preferred embodiment, the initiator polymer includes one or more initiator groups that allow for intra- or intermolecular hydrogen abstraction reactions or photosensitization reactions utilizing photoreducible or photo-oxidizable dyes when activated. Useful energy transfer acceptors or reductants for use with these types of initiators include, but are not limited to, tertiary amines such as triethanolamine, triethylamine, N-methyl diethanolamine, N,N-dimethyl benzylamine, tetramethyl ethylenediamine; secondary amines such as dibenzyl amine, N-benzyl ethanolamine, N-isopropyl benzylamine; and primary amines such as ethanolamine, lysine, and ornithine.

In one embodiment, photoinitiator groups having an absorbance of 350 nm and greater are used. More preferably, photoinitiator groups having an absorbance of 500 nm and greater are used. Suitable photoinitiator groups include light-activated initiator groups, such as long-wave ultra violet (LWUV) light-activatable molecules and visible light activatable molecules. Suitable long-wave ultra violet (LWUV) light-activatable molecules include, but are not limited to, ((9-oxo-2-thioxanthanyl)-oxy)acetic acid, 2-hydroxy thioxanthone, and vinyloxymethylbenzoin methyl ether. Suitable visible light activatable photoinitiator groups include, but are not limited to, acridine orange, camphorquinone, ethyl eosin, eosin Y, erythrosine, fluorescein, methylene green, methylene blue, phloxime, riboflavin, rose bengal, thionine, and xanthine dyes.

One common feature on these visible light activatable photoinitiator groups, and photoinitiator groups in general, is that of having a nonpolar portion. Due to the presence of this nonpolar portion, these photoinitiator groups generally have a low solubility in aqueous solutions. When these photoinitiator groups are coupled to another molecule, such as an initiator polymer, the photoinitiator groups can confer nonpolar characteristics to the polymer and can generally reduce its solubility in an aqueous solution.

The initiator polymer contains a number of initiator groups in an amount sufficient to promote free radical polymerization of polymerizable material on the surface of a substrate, such as the surface of a biological material. The initiator polymer contains at least one and more typically a plurality of initiator groups. In some cases, the initiator polymer is highly loaded with initiator groups and can provide a high level of polymerization initiator activity. This arrangement may be desirable in methods or compositions that include macromers that do not readily polymerize to form a polymeric layer. Accordingly, the invention provides positively-charged initiator polymers that are highly loaded with initiator groups.

Therefore, in one embodiment, the initiator polymer includes at least one initiator group. In more preferred embodiments the initiator polymer includes 5 or more initiator groups, and in even more preferred embodiments the initiator polymer includes about 10 or more initiator groups. In even more preferred embodiments, the initiator polymer has a Mw of $3.2 \times 10^6$ Da or less, most preferably 250,000 Da or less, and includes 5 or more initiator groups, and more preferably about 10 or more initiator groups. The initiator groups can be pendent along the polymer backbone at any position and can be spaced in a random or ordered manner.

The initiator group can be coupled to the initiator polymer using any suitable method. In one method, for example, polymerizable monomers having initiator groups can be synthesized and subsequently used in a polymerization reaction to create an initiator polymer with pendent initiator groups. Synthesis of initiator-derivatized monomers can be readily accomplished using standard chemical reactions. For example, an acid chloride analog of a photoinitiator group, such as a light-activated dye, can be reacted with an ethylenically unsaturated amine-containing monomer to form an initiator-derivatized monomer. In another method of preparing the initiator polymer, preformed polymers having reactive groups are reacted with initiator groups to attach the initiator groups to the preformed polymer. For example, an isothiocyanate or an acid chloride analog of a photoinitiator can be reacted with a polymer containing pendent amine groups thereby forming an initiator polymer bearing pendent initiator groups. Other synthetic schemes known to those of skilled in the art can be employed to prepare the initiator polymer. These schemes are contemplated but will not be discussed in further detail.

In preferred embodiments the initiator polymer includes a plurality of initiator groups that are nonpolar. The presence of a plurality of nonpolar initiator groups can confer substantial hydrophobic properties to the initiator polymer. Accordingly, this substantial hydrophobic property can be counter balanced by providing the initiator polymer with a cationic portion, which is discussed in greater detail below.

The positive charge of the cationic portion of the initiator polymer can be contributed by the backbone of the initiator polymer, by positively-charged groups pendent from the backbone, or both. In one embodiment, the initiator polymer has a plurality of cationic groups pendent from the backbone of the initiator polymer; preferably the cationic groups are provided by ternary or quaternary cationic moieties, such as quaternary amine groups. In another embodiment the polymeric backbone contains nitrogen and can be, for example, a polymeric imine. According to preferred embodiment of the invention, the cationic portion can provide the initiator polymer with a positive charge allowing for solubility in an aqueous solution and/or the ability to interact with a negatively charged surface.

The cationic portion that provides a positive charge to the initiator polymer in conditions having a pH at least up to, and including, pH 8 is particularly advantageous in embodiments wherein the initiator polymer includes a plurality of nonpolar initiator groups. The hydrophobic properties conferred by the nonpolar initiator groups can be counteracted by the presence of a cationic portion present on the initiator polymer, which can improve the solubility of the initiator polymer in aqueous solutions. According to the invention, the cationic portion is arranged to allow the initiator polymer to be soluble in aqueous solution and is also arranged to allow the initiator polymer to interact with a negatively charged surface, such as the surface of a cell. The cationic portion is arranged to provide a positive charge to the initiator polymer in environments having a pH at least up to, and including pH 8; and in some aspects the cationic portion is arranged to provide a positive charge to the initiator polymer in environments having a pH at least up to, and including, pH 10, and more preferably in environments having a pH at least up to, and including, pH 12.

In order to determine whether the initiator polymer maintains a positive charge in conditions having a pH of up to, and including, pH 8, any one of a number of tests can be performed. A suitable test for a positively-charged initiator polymer can generally involve preparing a buffered solution having a pH of 8, or higher than 8, adding the initiator polymer to the buffered solution, placing the polymer solution in contact with a material that provides a negative charge, and then determining whether the initiator polymer interacts with the negatively charged material. For example, an initiator polymer can be added to a solution that has been adjusted to a pH of 8 or greater with a suitable high-pH buffer such as tris (hydroxymethyl)aminomethane, ammonium bicarbonate, or 3-(cyclohexylamino)-1-propanesulfonate; the polymer mixture can then be applied to an anionic exchange matrix (for example, Q-Sepharose; Amersham Biosciences Corp., Piscataway, N.J.); the column can then be washed with the high-pH buffer; finally, the column can be eluted with a salt-containing buffer (such as 0.5 M NaCl) to dissociate the initiator polymer, if bound. If the initiator polymer maintains a positive charge in the selected buffer conditions, it will be present and detectable by spectroscopy in the eluate. Other commonly used analytical methods useful for determining the charge of the initiator polymer in a solution having a pH of 8 or more are contemplated and will not be discussed further.

In some embodiments, the initiator polymer has a polymeric backbone that is coupled to at least one and more typically a plurality of cationic groups. The polymer backbone, which generally refers to the polymer chain without addition of any initiator group or cationic group, typically includes carbon and preferably one or more atoms selected from nitrogen, oxygen, and sulfur. The backbone can include carbon-carbon linkages and, in some preferred embodiments, can also include one or more of amide, amine, ester, ether, ketone, peptide, or sulfide linkages, or combinations thereof. Examples of suitable polymer backbones include polyesters, polycarbonates, polyamides, polyethers (such as polyoxyethylene), polysulfones, polyurethanes, or copolymers containing any combination of the representative monomer groups.

The polymeric backbone can include reactive groups useful for the coupling of cationic groups to form the initiator polymer. Suitable reactive groups include acid (or acyl) halide groups, alcohol groups, aldehyde groups, alkyl and aryl halide groups, amine groups, carboxyl groups, and the like. These pendent reactive groups can be used for the coupling the initiator group and, in some embodiments, for the coupling of the cationic groups to the polymeric backbone. These chemical groups can be present either on a preformed polymer or on monomers used to create the positively-charged initiator polymer. Examples of polymers having suitable reactive or charged side group include polymers, and in particular dendrimers, having reactive amine groups such as polylysine, polyornithine, polyethylenimine, and polyamidoamine.

In one embodiment of the invention, the backbone of the initiator polymer provides an overall positive charge and contributes to the cationic portion. An example of this type of polymeric backbone includes polymers having imine linkages, such as polyimines that also include primary, secondary, or tertiary amine groups. Use of these types of polymers in the synthesis of the initiator polymer are preferred as they can provide a highly derivatizable preformed polymer backbone to which a plurality of cationic groups and initiator groups can be coupled. Polyamines that are particularly suitable as a starting polymer for the synthesis of the initiator polymer include polyethylenimine, polypropylenimine, and the like, and polyamine polymers or copolymers, and in particular dendrimers, formed from monomers such as the following amine functional monomers: 2-aminomethylmethacrylate, 3-(aminopropyl)-methacrylamide, and diallylamine. Suitable polyamines are commercially available, for example, Lupasol™ PS (polyethylenimine; BASF, New Jersey).

In preferred embodiments of the invention, the backbone of the initiator polymer is coupled to one or more cationic groups. Preferred cationic groups have a stable positive charge and include ternary and quaternary cationic groups. Preferred cationic groups include quaternary ammonium, quaternary phosphonium, and ternary sulfonium. These types of cationic groups can provide the initiator polymer with a positive charge in a wide range of pH conditions, particularly in higher pH conditions wherein other cationic groups can become deprotonated and lose their positive charge. The positive charge on these initiator polymers is maintained at least in conditions having a pH up to, and including, pH 8; and in some aspects in conditions having a pH up to, and including, pH 10, and in some aspects in conditions having a pH up to, and including, pH 12.

As indicated, preferred cationic groups include quaternary ammonium, ternary sulfonium, and quaternary phosphonium groups. These groups can be provided in, for example, alkylated or alkoxylated forms having, for example, in the range of 1-6 carbons on each chain. Examples include, but are not limited to tetraalkylammonium, tetraalkoxyammonium, trialkylsulfonium, trialkoxysulfonium, tetraalkylphosphonium, and tetraalkoxyphosphonium cations. Specific examples include tetramethylammonium, tetrapropylammonium, tetrabenzylammonium and the like.

The cationic groups can be spaced in a random or ordered pattern along the length of the polymer backbone or can be present primarily on one end of the polymer backbone if desired. The initiator polymer can also include different combinations of cationic groups if desired.

The number of cationic groups pendent on the polymer backbone can be arranged to provide a functional initiator polymer. The function of the initiator polymer can include its solubility in an aqueous solution, its ability to associate with a surface, and its potency as a polymerization initiator. In one aspect, the cationic groups are present in an amount sufficient to solubilize the initiator polymer in an aqueous solution. In another aspect the cationic groups are present in an amount sufficient to allow for the interaction of the initiator polymer with a biological surface. According to the invention, the initiator polymer has at least one monomeric unit that is coupled to a cationic group; more preferably the initiator polymer has about 20% or more of its monomeric units coupled to cationic groups, and most preferably the initiator polymer has about 50% or more of its monomeric units coupled to cationic groups. When a plurality of nonpolar initiator groups are present, the initiator polymer can be arranged with a cationic portion that provides sufficient solubility and that can also be localized to a cell surface. This can be achieved by preparing an initiator polymer that has a defined ratio of initiator groups to cationic groups. Therefore, in one embodiment of the invention, the ratio of cationic groups:initiator groups on the initiator polymer is at least 1:1. In a more preferred embodiment this cationic group:initiator group ratio is at least 2.5:1, and most preferred embodiment ratio is at least 5:1.

In a preferred embodiment, the invention provides an initiator polymer having a positively-charged backbone and a plurality of quaternary amine groups pendent from the positively-charged backbone. The hydrophilic backbone can be a polymeric imine backbone and can have a plurality of quaternary amine groups pendent from the amine-containing backbone. In this embodiment, the presence of the quaternary amine groups allows the initiator polymer to retain a positive charge despite any fluctuations in the pH of the solution, and maintain the solubility of the initiator polymer in solution.

An initiator polymer having an initiator group and a cationic group can be prepared a variety of ways. For example, the initiator group and the cationic group can be attached to a "preformed" polymer or a copolymer that is reactive with the initiator and cationic groups. The preformed polymer or copolymer can be obtained from a commercial source or be synthesized from the polymerization of a desired monomer or combination of different monomers. In one example of preparing the initiator polymer, the initiator groups and the cationic groups are reacted with and attached, for example, by covalent bonding, to chemical groups pendent from the backbone of the polymer or copolymer. Such attachments of the initiator groups and the cationic groups can be achieved by, for example, substitution or addition reactions.

In one preferred embodiment of the invention, the initiator polymer is prepared using a highly derivatizable preformed polymer as the polymer backbone. Preferred polymers contain a high number of reactive (derivatizable) groups, such as primary amine groups, relative to the molecular weight of the polymer. Suitable polymers and copolymers include amine-containing polymeric units such as polyimines, for example, polyethylenimine. Use of these types of polymers or copolymers as backbones for the initiator polymer allows for the preparation of low and medium molecular weight initiator polymers that can be highly loaded with initiator groups and cationic groups.

In another method of preparing the initiator polymer, polymers having primary, secondary, tertiary amines, or combinations thereof, can be quaternized, resulting in the formation of charged quaternary amine groups on the polymer. For example, amines can be successively alkylated, by, for example, alkyl halides, to provide a quaternary amine via the Menshutkin reaction. In another useful method of synthesizing the initiator polymer, polymers having tertiary amines can be reacted with a photoinitiator derivatized with a benzyl halide, for example. This reaction allows for the coupling of the photoinitiator to the polymer and at the same time converting the tertiary amine group to a charged quaternary amine group.

In yet another method of preparing the initiator polymer, monomers having initiator groups and monomers having cationic groups are first prepared. These initiator and cationic group-containing monomers are then co-polymerized to create an initiator polymer coupled to both initiator and cationic groups. In some embodiments an individual monomer having both an initiator group and a cationic group can be used to prepare the initiator polymer. Optionally, other monomers that are not coupled to either an initiator or a cationic group can be polymerized with the cationic and the initiator-coupled monomers to create the initiator polymer. Methods of preparing the initiator polymer are exemplified below. Other standard methods known to those of skill in the art to prepare the initiator polymer are contemplated and will not be discussed further.

In one embodiment, the initiator polymer of the current invention is generally of a size sufficient to allow for its association with a biological surface and promote the polymerization of macromers on the biological surface upon its activation. In one preferred embodiment of the invention, low and medium molecular weight initiator polymers are used in cell encapsulation processes. Low and medium molecular weight initiator polymers are referred to as having $M_w$ of less than $3.2 \times 10^6$ Da, while high molecular weight polymers are referred to as having a $M_w$ of $3.2 \times 10^6$ Da and greater.

Therefore, in one preferred embodiment, the invention provides initiator polymers having a (i) a polymerization initiator group, (ii) a cationic portion that provides a positive charge to the polymer in conditions at least up to pH 8, and (iii) a $M_w$ of less than $3.2 \times 10^6$ Da. In more preferred embodiments the initiator polymer has a $M_w$ of about 250,000 Da or less, 100,000 Da or less, and 50,000 Da or less. In another preferred embodiment, the initiator polymers have a $M_w$ in the range from 3400 to about 250,000 Da, more preferably in the range from 8500 to about 250,000 Da, even more preferably in the range from 8500 to about 100,000 Da, and most preferably in the range from 8500 to about 50,000 Da. In another embodiment, the initiator polymer is up to about 1000 monomeric units, and typically in the range of about 25 to about 500 monomeric units.

The initiator polymer typically promotes the polymerization of polymerizable material, such as macromers, on a surface, thereby forming a matrix of polymeric material on the biological surface. The polymerizable material can be any sort of compound, including monomers and polymers having one or more polymerizable groups. Polymerizable groups are portions of the polymerizable compounds that are able to propagate free radical polymerization, such as carbon-carbon double bonds. Preferred polymerizable groups are found in polymerizable compounds having vinyl or acrylate groups. More specific polymerizable portions include acrylate groups, methacrylate groups, ethacrylate groups, 2-phenyl acrylate groups, acrylamide groups, methacrylamide groups, itaconate groups, and styrene groups. Preferred materials for the encapsulation of cellular material are biocompatible polymerizable polymers (also referred to as macromers). Such macromers can be straight chain or branched polymers or copolymers, or graft copolymers. Synthetic polymeric macromers, polysaccharide macromers, and protein macromers suitable for use with the initiator polymer of the current invention are described in U.S. Pat. No. 5,573,934 (Hubbell et al.), the teaching of which is incorporated in its entirety by reference.

Preferred macromers include, but are not limited to, polymerizable poly(vinylpyrrolidone) (PVP), poly(ethylene glycol) (PEG), poly(ethylene oxide) poly(ethyloxazoline), poly (propylene oxide), polyacrylamide (PAA), poly(vinyl alcohol) (PVA), copolymers thereof, and the like. In particular, PEG and PAA are more preferred macromers. These types of macromers are typically soluble in water and are more stable in vivo as compared to biodegradable polymers.

In some cases it may be desirable to use naturally occurring or synthetic macromers as the polymerizable material. Suitable macromers include naturally occurring polymers such as polysaccharides, examples of which include, but are not limited to, hyaluronic acid (HA), starch, dextran, heparin, and chitosan; and proteins (and other polyamino acids), examples of which include, but are not limited to, gelatin, collagen, fibronectin, laminin, albumin and active peptides thereof. In order to make these naturally occurring or synthetic macromers polymerizable, polymerizable groups can be incorporated into a polymer using standard thermochemical reactions. For example, polymerizable groups can be added to collagen via reaction of amine containing lysine residues with acryloyl chloride. These reactions result in collagen containing polymerizable moieties. Similarly, when synthesizing a macromer, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups. Suitable synthetic polymers include hydrophilic monomers containing degradable segments as described in U.S. Pat. No. 5,410,016 supra, the teaching of which is incorporated in its entirety by reference.

In another aspect, the invention provides a polymerizable composition that includes a positively-charged initiator polymer and a macromer. The polymerizable composition can also include other compounds useful in cell encapsulation methods such as reductant/acceptors and viscosity-enhancing agents. Suitable viscosity-enhancing agents include, for example, polyethylene glycols (PEGs), and glycerol. Therefore, in one embodiment, the invention provides a polymerizable composition that includes: (i) an initiator polymer having at least one polymerization initiator group, and a cationic portion that provides a positive charge to the polymer in conditions having a pH at least up to, and including, pH 8 and (ii) a macromer. In a more specific embodiment the invention provides a polymerizable composition that includes: (i) a photoinitiator group selected from the group of visible light-activated dyes, and (ii) a cationic portion that provides a positive charge to the polymer in conditions having a pH at least up to, and including, pH 8.

As previously indicated, the initiator polymer of the invention is typically used with macromers and, in some cases, a reductant/acceptor in a method to provide a coating to a biological surface. The reagents are particularly suitable for cell encapsulation processes.

Cells or tissue to be encapsulated can be obtained directly from an organism, such as a mammal. Alternatively cells can be obtained from a cell culture. The cells intended for encapsulation can be transformed or otherwise modified. Specific types of cells and tissue that can be encapsulated and used for the treatment of diseases are discussed below. "Cells" refers to individual membrane-bound biological units that can be present as part of a tissue or organ, or can function independently as micro-organisms. "Tissue" refers to a biological mass that includes groups of similar cells, and also typically includes extracellular material that is associated with the cells. Cells, or tissue in particular, can be subject to treatment prior to the encapsulation process. For example, tissue can be treated with enzymatic or other suitable reagents, such as trypsin, hyaluronidase, or collagenase, to obtain individual cells or cell groups of a suitable size for the encapsulation process. Alternatively, tissue can be subject to mechanical processes in order to prepare suitable cellular starting material. Prior to the encapsulation process, cells can also be treated with drugs, prodrugs, hormones, or the like, or can be cultured to provide cells that display a desired expression pattern or have certain morphological features. Technical references that provide detailed instructions for the preparation of cells or tissue and the treatment of prepared cells or tissue are available and can be found in, for example, in Pollard, J. W. and Walker, J. M. Ed., *Basic Cell Culture Protocols* (1997). Alternatively, cells or tissue suitable for encapsulation and intended for use with the positively-charged initiator of the invention can be commercially obtained. For example, viable human liver preparations such as microsomes and hepatocytes, and viable human pancreatic preparations, such as pancreatic islets can be obtained from commercial sources such as CellzDirect, Inc. (Tucson, Ariz.).

With information available in technical literature, one can utilize the positively-charged initiator polymer in methods for coating a surface, and in particular, in the novel and inventive methods provided herein, for encapsulating cells and tissue. For example, the teaching of Cruise, et al., *Cell Transplantation* 8:293 (1999), can provide a basis for the cell encapsulation methods using the positively-charged polymerization initiator of the invention. Cells or tissue suitable for the encapsulation process, prepared as indicated above or obtained from a commercial source, can be suspended in a suitable media, such as a biocompatible buffered aqueous media, such as, for example Roswell Park Memorial Institute (RPMI) media. Other reagents can be added to this solution, such as animal serum; proteins such as albumin; oxidants; reductants; vitamins; minerals; growth factors; or other components that can have an impact on the viability and function of the cells or tissues as desired.

The positively-charged initiator polymer can be added to this solution before or after contacting the cells or tissue with the solution. The initiator polymer can be brought into contact with the cells in an amount that is sufficient to facilitate formation of a matrix around the cells or tissue. In one embodiment, the concentration of the initiator polymer is from 0.001 to 0.5 wt %. In yet another embodiment, the concentration of the initiator polymer is from 0.1 to 0.25 wt %. In one embodiment the initiator polymer is brought in contact with the cells for a period of time that is sufficient for the initiator polymer to associate with the surface of the cells. Optionally, a washing step can be performed. This washing step can be used, for example, to remove excess, unbound initiator or other material in contact with the cells. After the initiator polymer is brought in contact with the cells or tissue, the polymerizable material, such as macromers, can be brought in contact with the cells. In another embodiment, the initiator polymer is brought into contact with the cells or tissue together with the polymerizable material. In yet another embodiment the polymerizable material is brought into contact with the cells prior to bringing the initiator polymer into contact with the cells.

The polymerizable material (for example, macromers) can be brought into contact with the cell or tissue in an amount that allows formation of a matrix of a desired thickness. A concentration of macromer in solution useful for cell encapsulation can be in the range of 5-50 wt %, and more preferably in the range of 10-30 wt %. In some embodiments, the polymerizable material can be placed in contact with the cells for a period of time prior to activating the positively-charged initiator polymer.

Other reagents can be brought in contact with the cells or tissue during the encapsulation process. As previously mentioned, such reagents include acceptors or reductants, such as tertiary amines (for example, triethanolamine) that can form a free radical and cause free radical polymerization of the polymerizable material. Suitable acceptors or reductants are known in the art and are commercially available. These acceptors or reductants are typically used in indirect polymerization methods wherein the initiator group transfers energy to the acceptors or reductants to promote free radical polymerization of the polymerizable material. Reagents such as viscosity-enhancing reagents can also be used in the method of the invention. Viscosity-enhancing reagents can improve the process of polymerization. Suitable acceptors or reductants are known in the art and are commercially available. One of skill in the art can determine suitable amounts of any of these additional reagents for performing the encapsulation process.

After the reagents necessary to promote formation of a matrix are brought in contact with the surface to be coated, a source of energy, such as a thermal or electromagnetic energy sufficient to activate the initiator group, is applied to initiate polymerization of the polymerizable material. Long-wave ultra violet (LWUV) and visible wavelengths in range of 350 nm to 900 nm are preferred and can be supplied by lamps and laser light sources. Lamps or laser light sources that can provide these wavelengths of light are commercially available and can be obtained from, for example, EFOS, Inc. (Mississauga, Ontario, Canada). A particularly suitable wavelength for use with the preferred initiator polymers of the invention is about 520 nm. The time and temperature of the reaction are maintained to provide a desired coating. For example, the cells or tissue in contact with the initiator polymer and macromer can be treated with light for a period in the range of seconds to minutes. The polymerization reaction can be terminated by removing the light source. The encapsulated cells or tissue can then be subject to further treatment if desired. For example, it may be desirable to concentrate the encapsulated material, for example, by centrifugation, prior to introducing the encapsulated material into a subject.

As indicated, a number of technical references that provide detailed procedures for encapsulating cells are available and can provide a framework for which the positively-charged initiator polymer can be used. Therefore, using the available information, one can perform surface coating of a material, more specifically, the encapsulation of cellular material and tissue using the positively-charged initiator polymer and reagents described herein or in other references.

According to the invention, the polymerization initiator can be used to promote the formation of a matrix of polymerized material on a biological surface. Polymerization using the polymerization initiator can be performed in vivo by applying a polymerization initiator and polymerizable material, either together or separately, to a subject in either invasive or noninvasive procedures. Other particularly useful applications involve the ex vivo encapsulation of cells or tissue. In this application cells or tissue can be obtained from a suitable source, encapsulated with a matrix of polymeric material using a composition including the initiator polymer described herein, and then introduced into a subject in need of the encapsulated cells or tissue. This type of ex vivo encapsulation and transplantation procedure is advantageous as it can provide a matrix coating affording the transplanted cells protection from host immune rejection yet allowing the encapsulated cells to provide a therapeutic value to the host. In some cases, after receiving the transplanted encapsulated cells, the subject can be administered a pharmaceutical agent that can penetrate the polymeric layer that encapsulates the cells and can provoke a cellular response, which is of therapeutic value to the subject.

In one aspect of the invention, the initiator polymer is used to encapsulate cells or tissue from glands and organs of the endocrine system, which include cells from the pituitary gland; cells from the adrenal gland; cells from the thyroid/parathyroid glands; cells from the pancreatic islets, such as beta cells, alpha cells, delta cells, and pancreatic polypeptide (PP) cells; cells from the liver; and cells from reproductive glands such as the testis and ovary. Endocrine cells can be removed from a donor individual and encapsulated with polymeric material using the initiator polymer as described herein.

Encapsulated endocrine cells can be transplanted to an individual having any of the following conditions or needs: a pituitary disorder and in need of growth hormone (GH), adrenocorticotropic hormone (ACTH), follicle stimulating hormone (FSH), leutinizing hormone (LH), thyroid stimulating hormone (TSH), oxytocin, or antidiuretic hormone (ADH); an adrenal disorder and in need of mineral corticoids (for example, aldosterone) glucocorticoids (for example, cortisol), androgenic steroids, or catecholamines such as epinephrine or norepinephrine; a thyroid or parathyroid disorder and in need of thyroxin, calcitonin, or parathyroid hormone (PTH); a pancreatic disorder such as diabetes and in need of insulin, glucagon, somatostatin, or pancreatic polypeptide; a liver disorder and in need of bile or plasma proteins, including clotting factors; a reproductive gland disorder and in need of male hormones such as testosterone or female hormones such as estrogen.

Other types of cells that can be encapsulated include immature and mature cells from the cardiovascular, respiratory, renal, nervous, muscular, and skeletal systems. In some aspects cells that have been transformed or genetically modified can be encapsulated and transplanted into a host. For example, cells that have been transformed or modified to produce a therapeutically useful compound, such as a peptide hormone or an enzyme can be encapsulated and introduced into an individual.

The initiator polymer and polymerizable material can also be used in in vivo applications to provide artificial barriers, for example, barriers to prevent tissue adhesion following surgery. For this application, the initiator polymer along with polymerizable material is applied to the surface of the tissue. The composition is then illuminated to initiate polymerization and formation of the barrier matrix. The polymeric matrix prevents other tissue from adhering to the coated tissue. In some procedures a polymeric matrix can be formed on the surface of a blood vessel to prevent blood factors or cells, such as platelets, from interacting with or adhering to the blood vessel wall. Both degradable and non-degradable macromer systems can be used for this purpose.

As stated above, in some instances, a pharmaceutical agent can be administered to the subject after receiving the encapsulated cells. The pharmaceutical agent can provoke a therapeutically useful cellular response from the encapsulated cells if needed. Other useful drugs that can be administered to subjects having encapsulated cells include antithrombogenic, anti-inflammatory, antimicrobial, antiproliferative, and anticancer compounds, as well as growth factors, morphogenic proteins, and the like.

The invention will now be demonstrated referring to the following non-limiting examples.

EXAMPLES

Example 1

Synthesis of APTAC-Polyethylenimine (APTAC-PEI) Polymer

As starting material for the preparation of a photoinitiator polymer, a positively-charged polymer having a polyethylenimine backbone coupled to cationic quaternary ammonium groups was prepared.

Quaternary ammonium groups, in the form of (acrylamidopropyl)trimethyl-ammonium chloride molecules were coupled to a polyethylenimine polymer using the following procedure: Five grams of polyethylenimine (10,000 $M_w$; Polysciences, Warrington, Pa.) were dissolved in 10 ml of deionized water to make a 50% PEI solution. To the 50% PEI solution was added 16 g of a 75% (3-acrylamidopropyl)-trimethylammonium chloride solution (APTAC; Simga-Aldrich Corp., St. Louis, Mo.). The mixture of PEI and APTAC was shaken overnight at 55° C. The resulting product was a viscous, amber-colored solution, which was stored in a sealed vial at room temperature.

Monitoring the vinyl protons of the APTAC molecule by NMR (Nuclear Magnetic Resonance) on a small scale reaction of equivalent concentrations used in the preparation of APTAC-PEI indicated the reaction was 99% complete at room temperature in 16 hours.

Using a 2.4:1 w/w ratio of APTAC to PEI (12 g APTAC to 5 g PEI (10,000 Da)) as described above, it was estimated that the final $M_w$ of APTAC-PEI was approximately 3.4 times greater (34,000 Da) than the $M_w$ of the starting PEI polymer (10,000 Da).

TABLE I

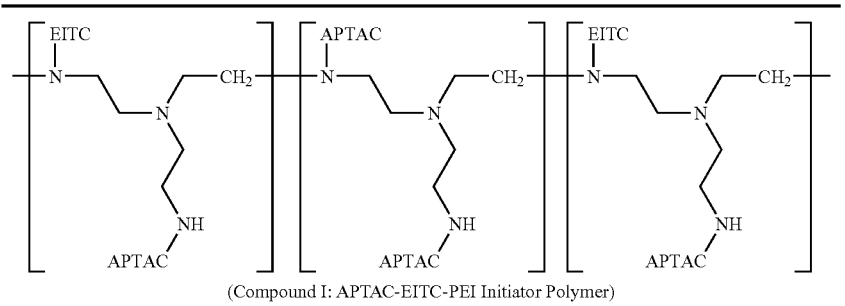

(Compound I: APTAC-EITC-PEI Initiator Polymer)

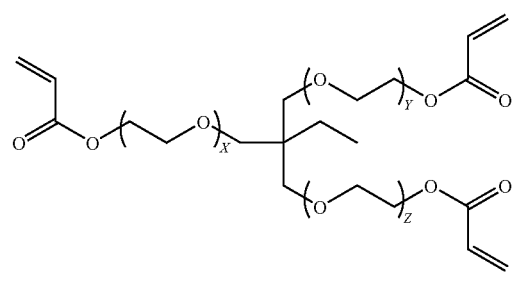

(Compound II: PEG-triacrylate macromer)

Example 2

Synthesis of APTAC-EITC-Polyethylenimine (APTAC-EITC-PEI) Initiator Polymer The positively-charged APTAC-PEI polymer synthesized in Example 1 was used as starting material for the preparation of a photoinitiator polymer having pendent photoinitiator groups.

The APTAC-PEI polymer (200 μl) as synthesized in Example 1 was dissolved in 5 ml of DMSO. Eosin-isothiocyanate (100 mg) (EITC; Helix Research, Springfield, Oreg.) was dissolved in 45 ml DMSO to make a 2.2 mM EITC solution. Solutions or reactions containing the EITC solution were subsequently performed in the dark or in light sealed containers. 5 ml of the APTAC-PEI/DMSO solution was mixed with 45 ml of the 2.2 mM EITC/DMSO solution and mixed for 24 hours at room temperature.

After 24 hours unreacted EITC was removed via ultrafiltration using two Biomax filters (5,000 $M_w$ cutoff (MWCO); Millipore Co. Billerica, Mass.) using 2,000 mls of a 20% DMSO, 80% water solution as a wash. The next wash was performed with 2,000 mls of 50 mM ammonium carbonate instead of the DMSO/water solution also using two 5,000 $M_w$ cutoff Biomax filters. 231 mg of APTAC-EITC-PEI polymer product was recovered by lyophilization and stored protected from light at room temperature. The final weight of the APTAC-EITC-PEI initiator polymer product was approximately 42.5 kDa.

A APTAC-EITC-PEI initiator polymer product can be represented by Compound I in Table I.

Example 3

Preparation of APTAC-EITC-PEI Initiator Polymers of Various Molecular Weights Using a procedure similar to that described in Examples 1 and 2, APTAC-EITC-PEI initiator polymers having variations in both (a) molecular weights and (b) EITC content were prepared.

PEI polymers having $M_w$s of 750,000 (750K) Da, 10,000 (10K) Da, 2,000 (2K) Da, and 800 Da were obtained from Polysciences, Warrington, Pa. To prepare PEI having 50% APTAC coupling, a 2.4:1 w/w ratio of APTAC to PEI for each different sized PEI polymer was used. In to prepare PEI having 20% APTAC coupling, a 0.96:1 w/w ratio of APTAC to PEI for each different sized PEI polymer was used. Reagents and reaction times as detailed in Example 1 were used for each of the preparations. Subsequently, preparations of APTAC-PEI polymers of the recited sizes were then coupled to EITC molecules using reagents and reaction times as detailed in Example 2. Specifically, each APTAC-PEI polymer preparation (200 μl) was dissolved in 5 ml of DMSO and mixed with 45 ml of the 2.2 mM EITC/DMSO solution and then mixed for 24 hours at room temperature. The purification steps as detailed in Example 2 were performed for each of the samples and the yields of each preparation was comparable to that of the recovery using the 10,000 $M_w$ PEI polymer of Examples 1 and 2.

According to the results it is calculated that the final $M_w$s of the initiators at a 50% APTAC target loading will be as follows:

Starting $M_w$ PEI (Da) Approximate Final $M_w$ APTAC-EITC-PEI (Da)

| Starting $M_w$ PEI (Da) | Approximate Final $M_w$ APTAC-EITC-PEI (Da) |
|---|---|
| (a) 800 | 3400 |
| (b) 2000 | 8500 |
| (c) 10,000 | 42,500 |
| (d) 750,000 | $3.2 \times 10^6$ |

Example 4

Preparation of APTAC-EITC-Dendrimer Initiator Polymers

Using a procedure similar to that described in Examples 1 and 2, PEI-APTAC-dendrimer initiator polymers were prepared. An amine functional dendrimer with a molecular weight of 14,215 Da was used as a polymer backbone in place of the 10,000 Da PEI used in examples 1 & 2.

As a first step in the synthesis of the dendrimer initiator polymer, an intermediate APTAC-dendrimer was made. One gram of ethylenediamine-core poly(amidoamine) dendrimer (PAMAM dendrimer, Generation 4, FW 14,215 Da, 10 wt % in methanol; Sigma-Aldrich, St. Louis, Mo.) was placed in a flask along with 44.7 mg of a 75% APTAC solution (Sigma-Aldrich). The methanol was removed on a rotary evaporator to give a residue of 176 mg and the residue was heated in an oven at 37° C. for 3.5 days. NMR analysis of the residue in deuterated methanol ($CD_3OD$) indicated the reaction was greater than 99% complete based on the vinyl protons of APTAC.

An APTAC-dendrimer/DMSO solution was prepared by dissolving 30 mg of the APTAC-dendrimer intermediate in 5 ml of DMSO. An EITC/DMSO solution was prepared by dissolving 25 mg of eosin-isothiocyanate (EITC; Helix Research, Springfield, Oreg.) in 300 microliters of DMSO. The dendrimer-APTAC/DMSO solution was combined with the EITC/DMSO solution and mixed for 24 hours at room temperature. Solutions or reactions containing EITC were performed in light-protected containers (amber-colored vials).

After 24 hours unreacted EITC was removed via ultrafiltration using two Biomax filters (5,000 $M_w$ cutoff (MWCO); Millipore Co. Billerica, Mass.) using 2 liters of a 20% DMSO, 80% water solution as a wash. The next wash was performed with 2 liters of 50 mM ammonium carbonate instead of the DMSO/water solution also using two 5,000 $M_w$ cutoff Biomax filters. 47 mg of APTAC-EITC-dendrimer product was recovered by lyophilization and stored protected from light at room temperature.

Example 5

Preparation of a Trimethylolpropane Ethoxylate (20/3 EO/OH) Triacrylate Macromer A PEG-based macromer was synthesized for use with the initiator polymers as detailed below.

Synthesis of the PEG-based macromer is illustrated in FIG. 1. Trimethylolpropane ethoxylate (PEG-triol; 100.0 g, 98.6 mmoles; Average $M_w$ ca. 1,104; Cat. No. 41,617-7; Aldrich Chemical Company, Inc., Milwaukee, Wis.) was dissolved in 200 mls of toluene with stirring and refluxed for one hour. The PEG-triol solution was allowed to cool to approximately 80° C. At this time, 50 mg (0.403 mmoles) of 4-methoxyphenol (MEHQ; J. T. Baker, Phillipsburg, N.J.), 42.7 g (0.592 moles) of acrylic acid (J. T. Baker, Phillipsburg, N.J.), and 10 mls (0.188 moles) of sulfuric acid (Aldrich Chemical Company, Inc., Milwaukee, Wis.) were added with stirring to the reaction solution. The reaction solution was heated to reflux. The reaction was allowed to progress until about 6.0 mls of water was produced and collected via a Dean & Stark receiver (approximately one hour). The reaction mixture was allowed to cool to 50° C. and poured into a solution of sodium bicarbonate (270 g in 2.5 liters of deionized water) with stirring. The organic layer was separated, washed with deionized water and dried over sodium sulfate. The PEG-triacrylate was isolated using a wiped film still (Pope Scientific, Inc., Saukville, Wis.).

A PEG-triacrylate macromer product is represented by Compound II in Table I.

Example 6

Cell Encapsulation Using APTAC-EITC-PEI Initiator Polymers

The positively-charged initiator polymers as prepared in Examples 1, 2, and 3 are used as polymerization initiators to provide an encapsulating polymeric coating on the surface of cells. The cell encapsulation procedure includes the following steps: (i) contacting cells with a solution containing the APTAC-EITC-PEI polymers as prepared in examples 1-3; (ii) contacting cells with a solution containing the PEG-triacrylate macromer of Example 4; (iii) treating the cells in contact with the macromer and initiator with an argon laser light source; and (iv) washing with phosphate buffered saline (PBS). Following these steps the cells are inspected to determine the quality of coating around the cells (via microscopic examination) and the cell viability (trypan blue exclusion or propidium iodide staining).

We claim:

1. Encapsulated cellular material comprising:
   cells comprising a polymeric layer around the cells, the polymeric layer comprising
   (a) polymerized material and
   (b) a positively-charged initiator polymer having a polymeric backbone comprising
      (i) at least five initiator groups pendent from the polymeric backbone, and
      (ii) a cationic portion comprising cationic groups pendent from the polymeric backbone, wherein the cationic groups provide a positive-charge to the positively-charged initiator polymer in conditions having a pH up to and including, pH 8, wherein the cationic groups of the cationic portion interact with negatively charged surface molecules on the cellular material to localize the positively-charged initiator polymer on the surface of the cellular material, and wherein the positively-charged initiator polymer has a ratio of cationic groups:initiator groups of at least 1:1.

2. The encapsulated cellular material of claim 1 wherein the positively-charged initiator polymer has a polymeric backbone that comprises nitrogen.

3. The encapsulated cellular material of claim 2 wherein the polymeric backbone comprises a polyimine backbone.

4. The encapsulated cellular material of claim 3 wherein the polymeric backbone comprises polyethylenimine.

5. The encapsulated cellular material of claim 1 wherein the cationic groups comprise a group selected from the group consisting of quaternary ammonium, quaternary phosphonium, and ternary sulfonium.

6. The encapsulated cellular material of claim 5 wherein the cationic groups comprise a quaternary ammonium group.

7. The encapsulated cellular material of claim 1 wherein the cationic groups provide a positive charge to the positively-charged initiator polymer in conditions having a pH up to, and including, pH 10.

8. The encapsulated cellular material of claim 7 wherein the cationic groups provide a positive charge to the positively-charged initiator polymer in conditions having a pH up to, and including, pH 12.

9. The encapsulated cellular material of claim 1 wherein the initiator groups comprise a photoinitiator.

10. The encapsulated cellular material of claim 9 wherein the photoinitiator has an excitation wavelength of 350 nm or greater.

11. The encapsulated cellular material of claim 10 wherein the photoinitiator has an excitation wavelength of 500 nm or greater.

12. The encapsulated cellular material of claim 11 wherein the photoinitiator is selected from the group consisting of acridine orange, camphorquinone, ethyl eosin, eosin Y, erythrosine, fluorescein, methylene green, methylene blue, phloxime, riboflavin, rose bengal, thionine, and xanthine dyes.

13. The encapsulated cellular material of claim 1 wherein the positively-charged initiator polymer has a $M_w$ of less than $3.2 \times 10^6$ Da.

14. The encapsulated cellular material of claim 13 wherein the positively-charged initiator polymer has a $M_w$ of 250,000 Da or less.

15. The encapsulated cellular material of claim 1 wherein the cellular material comprises a pancreatic islet cell.

16. The encapsulated cellular material of claim 1 wherein the positively-charged initiator polymer comprises monomeric units in the polymeric backbone, and 20% or more of the monomeric units are coupled to the cationic groups.

17. The encapsulated cellular material of claim 16 wherein 50% or more of the monomeric units are coupled to the cationic groups.

18. The encapsulated cellular material of claim 1 wherein the positively-charged initiator polymer has a ratio of cationic groups:initiator groups of at least 2.5:1.

19. The encapsulated cellular material of claim 18 wherein the positively-charged initiator polymer has a ratio of cationic groups:initiator groups of at least 5:1.

20. The encapsulated cellular material of claim 1 wherein the polymeric layer comprises polymerized macromers.

21. The encapsulated cellular material of claim 20 wherein the polymerized macromers comprise a polysaccharide macromer or a protein macromer.

22. The encapsulated cellular material of claim 20 wherein the polymerized macromers comprise a macromer selected from the group consisting of poly(vinylpyrrolidone) (PVP) macromers, poly(ethylene glycol) (PEG) macromers, poly (ethylene oxide) poly(ethyloxazoline) macromers, poly(propylene oxide) macromers, polyacrylamide (PAA) macromers, poly(vinyl alcohol) (PVA) macromers, and copolymers thereof.

* * * * *